(12) United States Patent
Fievet

(10) Patent No.: US 8,714,567 B2
(45) Date of Patent: May 6, 2014

(54) SKI BOOT THAT CAN SUPPORT AT LEAST PART OF A SKIER'S WEIGHT AND ASSOCIATED SKI BOOT/SKI ASSEMBLY

(76) Inventor: Hubert Fievet, La Massana (AD)

( * ) Notice: Subject to any disclaimer, the term of this patent is extended or adjusted under 35 U.S.C. 154(b) by 0 days.

(21) Appl. No.: 13/202,672

(22) PCT Filed: Mar. 1, 2010

(86) PCT No.: PCT/FR2010/050343
§ 371 (c)(1),
(2), (4) Date: Nov. 22, 2011

(87) PCT Pub. No.: WO2010/097560
PCT Pub. Date: Sep. 2, 2010

(65) Prior Publication Data
US 2012/0056391 A1    Mar. 8, 2012

(30) Foreign Application Priority Data
Feb. 27, 2009    (FR) ...................................... 09 51282

(51) Int. Cl.
*A63C 3/02*    (2006.01)
(52) U.S. Cl.
USPC ................ 280/11.36; 280/611; 2/22; 2/24; 128/882; 128/108.1
(58) Field of Classification Search
USPC ....................... 280/611–634, 11.36
See application file for complete search history.

(56) References Cited

U.S. PATENT DOCUMENTS

| | | | | |
|---|---|---|---|---|
| 4,408,600 A | * | 10/1983 | Davis | 602/16 |
| 4,872,665 A | * | 10/1989 | Chareire | 482/51 |
| 5,823,546 A | * | 10/1998 | White | 280/22.1 |
| 6,409,693 B1 | * | 6/2002 | Brannigan | 602/16 |
| 8,060,945 B2 | * | 11/2011 | Adarraga | 2/22 |
| 2010/0094188 A1 | * | 4/2010 | Goffer et al. | 602/23 |

FOREIGN PATENT DOCUMENTS

| | | |
|---|---|---|
| DE | 29 30 648 A1 | 2/1981 |
| DE | 30 12 716 A1 | 10/1981 |
| DE | 32 13 282 A1 | 10/1983 |

OTHER PUBLICATIONS

International Search Report, dated Dec. 1, 2010, from corresponding PCT application.

* cited by examiner

*Primary Examiner* — John Walters
*Assistant Examiner* — James Triggs
(74) *Attorney, Agent, or Firm* — Young & Thompson

(57) ABSTRACT

A ski boot (1) includes an inner boot (1.1) that is designed to accommodate the skier's foot and a leading shell (1.2) that surrounds the inner boot (1.1), making it possible to hold the skier's ankle in place. This boot (1) also includes a calf support (3) attached to the shell (1.2) that is designed to accommodate the skier's calf, and a thigh support (5) that forms an angle ($\alpha$) with the calf support (3) that is designed to accommodate the skier's thigh when the latter is in the bent position. Preferably, the boot includes a damping element (8, 23, 27) that is installed between the calf support (3) and the thigh support (5), as well as elements (25, 26) for adjusting the angle ($\alpha$) between the calf support (3) and the thigh support (5).

17 Claims, 3 Drawing Sheets

Figure 1:
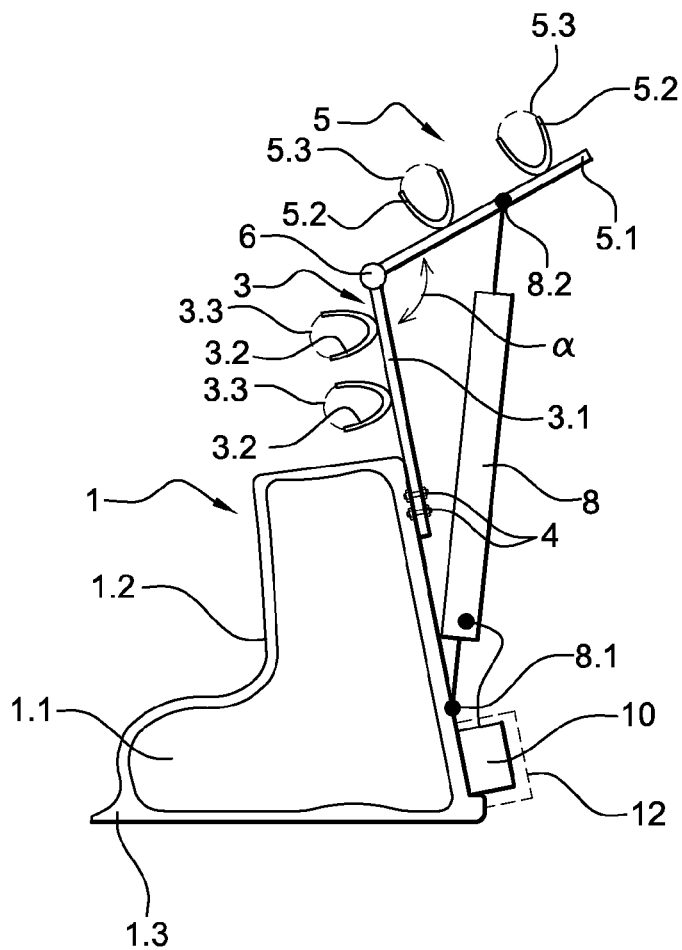

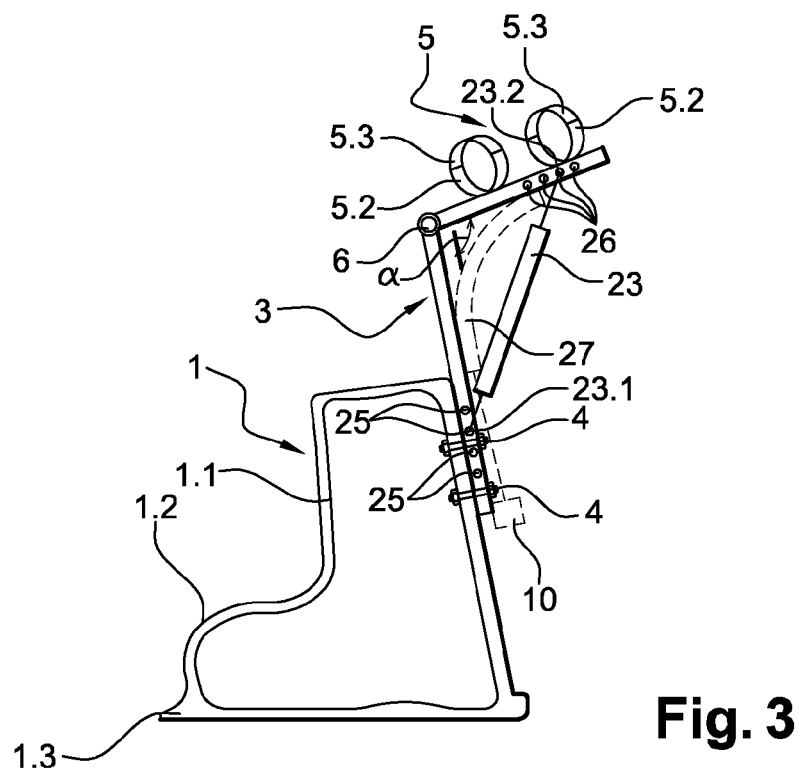
Fig. 3
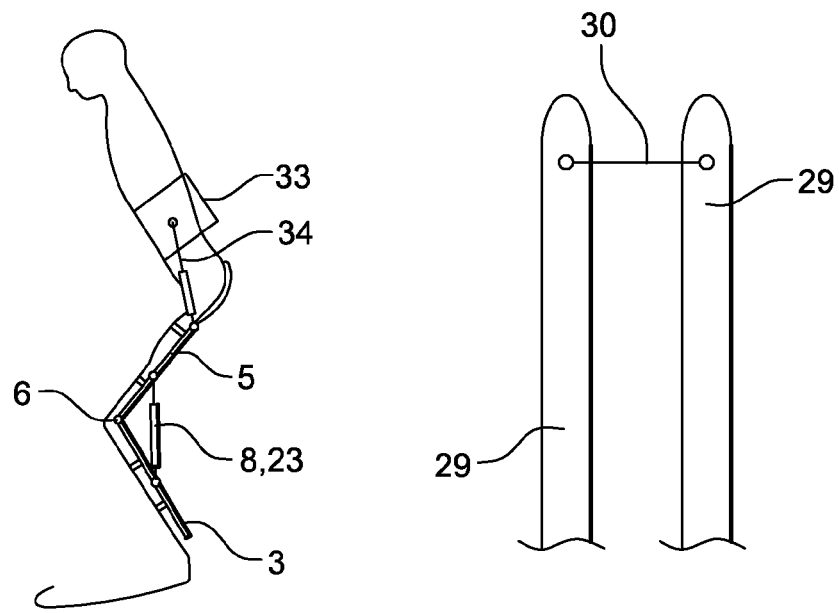
Fig. 4
Fig. 5

SKI BOOT THAT CAN SUPPORT AT LEAST PART OF A SKIER'S WEIGHT AND ASSOCIATED SKI BOOT/SKI ASSEMBLY

This invention relates to a ski boot that makes it possible to support at least part of a skier's weight and an associated set of ski boots and skis. The object of the invention in particular is to propose a ski boot that makes it possible to help the skier's legs support his weight.

The invention is designed in particular for individuals who have problems supporting their weight using their legs, such as individuals suffering from at least partial paralysis of the lower limbs, such as, for example, paraplegics, or tetraplegics, elderly individuals, or individuals suffering from multiple sclerosis. However, the invention can also be used by healthy individuals desiring to protect their lower limbs.

The invention finds a particularly advantageous application with downhill ski boots, but it could also be used with snowboard boots or surf shoes or any equipment that makes it possible to glide over snowy trails. The invention could also be used in the nautical field.

The invention starts from the feature that individuals who have problems supporting their weight with their legs cannot practice downhill skiing with the existing boots. Actually, these boots usually comprise an inner boot covered by a plastic shell that has over-molded protuberances that are designed to work with ski attachments. These boots that go up to the middle third of the leg only have the object of protecting the skier's ankle but does not make it possible to support his weight when he is supported on his skis.

There is therefore the need for a ski boot that helps the handicapped skier's legs support his weight when he is supported on his skis.

The invention fills this need by proposing a boot that comprises a calf support attached to the shell of the boot that is designed to hold the calf as well as a thigh support that forms an angle with the calf support that is designed to accommodate the skier's thigh when the skier is in a bent position. Preferably, the calf support is connected to the thigh support by means of a damping means that makes it possible, in addition to dampening the shocks, to compensate for the difference in height of the legs when the skier is perpendicular to the slope.

Thus, when the skier's leg is positioned inside the calf and thigh supports, a portion of the weight of the body is supported by the thigh support and the calf support, which relieves the skier's legs. In addition, with the thigh and the calf being held inside their respective supports, they cannot move very much relative to one another so that the skier's knee is protected.

Preferably, the damping means can be adjusted in height so as to allow an adjustment of the bending angle between the calf support and the thigh support.

The invention therefore relates to a ski boot that comprises an inner boot that is designed to accommodate the skier's foot and a leading shell that surrounds the inner boot, making it possible to hold the skier's ankle in place, characterized in that it also comprises:

A calf support attached to the shell that is designed to accommodate the skier's calf, and
A thigh support that forms an angle with the calf support that is designed to accommodate the skier's thigh when the latter is in the bent position,
The calf support and the thigh support being arranged between one another in such a way as to be able to support a portion of the skier's body.

According to one embodiment, with the thigh support being linked in movement relative to the calf support, it also comprises a damping means installed between, on the one hand, the shell of the boot, or the calf support, and, moreover, the thigh support.

According to one embodiment, it also comprises means for adjusting the bending angle between the calf support and the thigh support.

According to one embodiment, the damping means is formed by a double-action cylinder that has one end linked in rotation to the calf support or the shell of the boot and one end linked in rotation to the thigh support, whereby this cylinder is supplied by a compressed air distribution circuit.

According to one embodiment, the control means of the distribution circuit are control buttons or voice recognition means.

According to one embodiment, the damping means is formed by a single-action cylinder that makes it possible to raise the thigh support by the compressed air intake, with the cylinder then being lowered by the weight of the skier's body that expels the air from the cylinder.

According to one embodiment, the damping means is formed by a cylinder that is inflated in advance to a determined pressure with nitrogen or any other gas.

According to one embodiment, the means for adjusting the angle between the calf support and the thigh support are formed by a series of holes made along the length of the calf support and/or along the length of the thigh support, whereby the ends of the cylinder are each able to engage in one of the holes.

According to one embodiment, the damping means is formed by an air flange or any other flexible rod that is attached, on the one hand, to the calf support and, on the other hand, to the thigh support.

According to one embodiment, it is made of a single block with the thigh support and the calf support without a hinge between the two supports in such a way as to form a thigh boot, the material of this block playing the role of hinge and damper.

According to one embodiment, the calf support and the thigh support are equipped with at least one fabric strap to hold respectively the tibia and the thigh of the skier in position inside the supports.

According to one embodiment, the calf support rises as close as possible to the articular center of the knee.

According to one embodiment, the calf support is over-molded on the shell of the boot or molded together with the shell.

According to one embodiment, it also comprises a lumbar belt linked to the thigh support or to the calf support.

The invention also relates to a set, characterized in that it comprises boots according to the invention and skis that comprise means, such as a cord or a small chain, for limiting the gap between the skis.

The invention also relates to a ski that comprises a gliding blade—on which a front attachment and a rear attachment are mounted—that is designed to accommodate respectively the front part of the ski boot and the rear part of the ski boot, characterized in that the front attachment is connected by a hinge- or ball-joint-type mobile system to the boot to make it possible to lift the individual up again after a fall.

Figure 2:
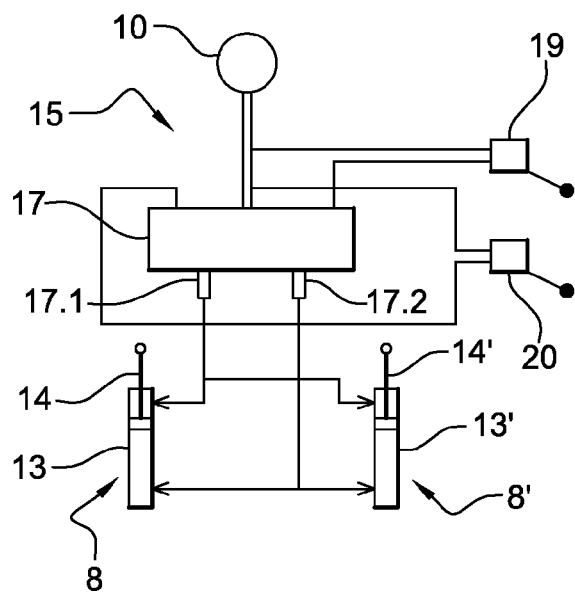

The invention will be better understood from reading the following description and from examining the accompanying figures. These figures are provided only by way of illustration but in no way limit the invention. They show:

FIG. 1: A side view of a first embodiment of a boot according to the invention;

FIG. 2: A diagrammatic representation of the control circuit of the cylinder used with the boot of FIG. 1;

FIG. 3: A side view of a second embodiment of a boot according to the invention;

FIG. 4: A side view of a variant embodiment according to the invention that makes it possible to support the top of the skier's body;

FIG. 5: A diagrammatic representation of skis according to the invention comprising means for limiting the gap between the skis.

Figure 6A:
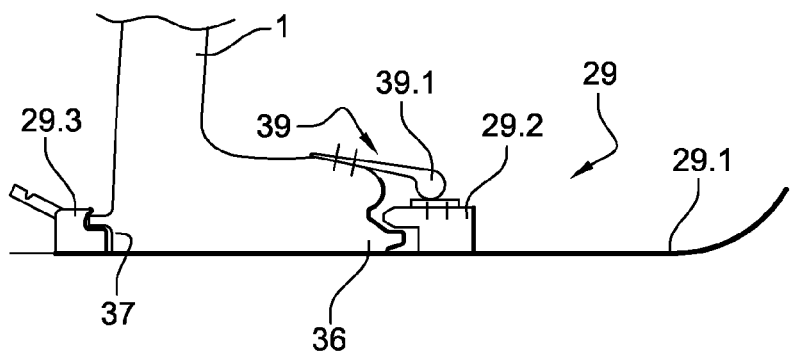
Figure 6B:
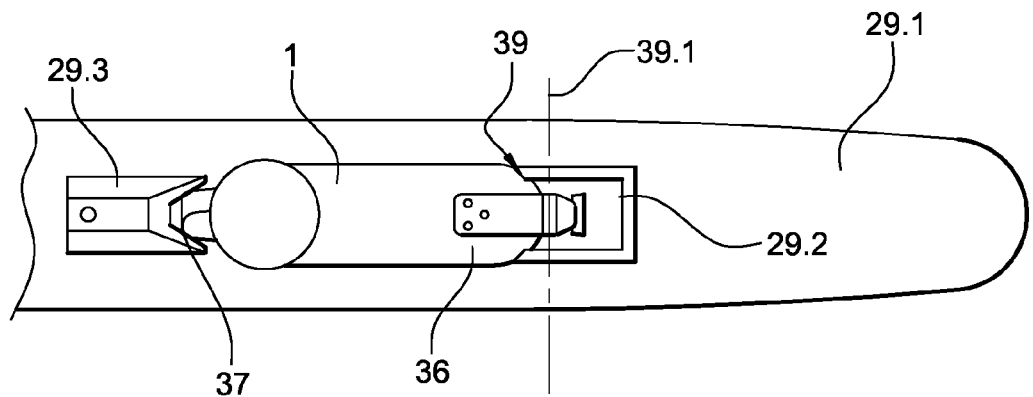

FIGS. 6a-6b: A side and top view of a ski according to the invention that is equipped with a hinge that is connected to the boot according to the invention.

Identical elements preserve the same references from one figure to the next.

FIGS. 1 and 3 show a ski boot 1 that comprises an inner boot 1.1 that is designed to accommodate the skier's foot and a plastic shell 1.2 that surrounds the inner boot comprising protuberances 1.3 that are designed to work with the ski attachments. This shell 1.2 is a leading shell so as to protect the skier's ankle.

The boot 1 according to the invention comprises a vertical calf support 3 that is attached to the shell 1.2 that is designed to accommodate the skier's calf. This calf support 3 rises as close as possible to the articular center of the knee. This support 3 is formed by, for example, a metal bar 3.1 (for example aluminum) that is attached to the shell 1.2 using attachment means 4 and arches 3.2 that extend transversely to the bar 3.1, whereby these arches 3.2 exhibit a shape that is complementary with the skier's calf. This support 3 can also comprise fabric straps 3.3 that make it possible to hold the skier's tibia in position in the arches 3.2. As a variant, the support 3 can be made of plastic or a composite material over-mounted on the shell 1.2 of the boot or molded at the same time as the shell 1.2.

The boot 1 also comprises a thigh support 5 that is linked in rotation relative to the calf support 3 along a horizontal axis 6 that is perpendicular to the direction of elongation of the ski. This support 5 that is designed to accommodate the skier's thigh forms a bending angle α with the calf support 3. This support 5 is formed by a longitudinal bar 5.1 that is movable in rotation relative to the calf support 3 and transverse arches 5.2 that have a shape that is complementary with the skier's thigh. As a variant, the support 5 is formed by two longitudinal bars that are movable in rotation relative to the calf support 3 and a trough in the shape of an arc extending between the two longitudinal bars. The support 5 can be made of metal, for example aluminum, which offers the advantage of being light, made of plastic or a composite material. The support 5 can also be equipped with fabric straps 5.3 that make it possible to hold the skier's thigh inside the arches 5.2.

In the embodiment of FIG. 1, a double-action cylinder 8 is installed between the thigh support 5 and a stationary part of the boot (the shell 1.2 or the calf support 3). Here, the cylinder 8 has one of its ends 8.1 linked in rotation relative to the shell 3.1 along an axis that is parallel to the axis 6 and the other of its ends 8.2 linked in rotation relative to the thigh support 5 along an axis that is parallel to the axis 6. As a variant, the end 8.1 could be attached to the calf support 3. This cylinder 8 is fed by a compressed air source 10 installed, for example, at the heel of the boot. This source 10 can be protected from shocks by means of a metal cage 12.

FIG. 2 shows the compressed air power circuit 15 of the two cylinders 8 and 8' of the ski boots, each comprising a body 13, 13' inside of which a piston 14, 14' moves in translation. This circuit 15 comprises a distributor 17 to which the pressure source 10 is connected. The air discharge 17.1 of the distributor 17 that makes possible the simultaneous descent of the cylinders 8, 8' is connected to the top part of the body of the two cylinders 8, 8', while the air discharge 17.2 of the distributor 17 that makes possible the simultaneous rise of the cylinders 8, 8' is connected to the low part of the cylinders 8 and 8'. The distributor 17 is controlled by control buttons 19, 20 (one for up, one for down), which are, for example, attached at the top of the leg support 5.

Thus, in operation, when the skier is in a bent position, the calf support 3 and the thigh support 5 support a part of the skier's body in such a way that the skier's legs are eased. And when the skier wants to have a higher bent position, he activates the button 19 in such a way that air penetrates the bottom of the body of the cylinders 8 and 8' simultaneously to make the pistons 14, 14' rise and incidentally to increase the angle α between the thigh support 5 and the calf support 3. As soon as the desired position is reached, the skier stops activating the button 19.

When the skier wants to have a lower bent position, he activates the button 20 in such a way that the air penetrates the top of the body of the cylinders 8 and 8' simultaneously to lower the pistons 14, 14' and incidentally to decrease the angle α between the thigh support 5 and the calf support 3. As soon as the desired position is reached, the skier stops activating the button 20.

It is noted that the system with double-action cylinders 8, 8' makes it possible for the individual who has fallen down to bring his legs back under him to be able to get up more easily by lowering the pistons of the cylinders 8, 8' by activating the control button 20.

As a variant, for handicapped individuals having problems in using their hands or for facilitating the control of the cylinders, the buttons 19, 20 are replaced by voice recognition means that can remotely control the distributor 17 via a radio connection. Thus, in one example, by saying the word "up," the skier can raise the cylinders 8, 8', while by saying the word "down," the skier can lower the cylinders 8, 8'. Preferably, these voice recognition means can be installed around the individual's body.

One skilled in the art will well understand that the damping effect is obtained by the air from the pistons 8, 8' that is compressed when the skier passes over bumps in such a way that the shocks are damped by the supports 3 and 5 of the skier's leg.

As a variant, the double-action cylinder 8 can be replaced by a single-action cylinder. The single-action cylinder makes it possible to raise the thigh support 5 by the compressed air intake, with the cylinder being lowered by the weight of the skier's body that expels the air from the cylinder.

As a variant, as shown in FIG. 3, the double-action cylinder 8 is replaced by a cylinder 23 that is inflated with nitrogen or any other gas. This type of cylinder is used in particular for car trunks. This cylinder 23 is calibrated in particular based on the skier's weight and the capability of his legs to support a portion of his weight. This cylinder 8 makes it possible to achieve a damping effect by the compression of the nitrogen that it contains. The pressure of the cylinder 8 can be modified at any time with suitable equipment.

Furthermore, the calf support 3 and the thigh support 5 are equipped with a series of holes, respectively 25 and 26, along their length so as to make possible the adjustment of the angle α between the support 3 and the support 5, with one of the holes 25, 26 of each series being designed to enter into cooperation with one of the ends 23.1, 23.2 of the cylinder 23. Thus, for increasing the angle α, the cylinder 23 is positioned between the holes 25, 26 that are positioned as close as possible to the pivot connection between the support 3 and the support 5; while for decreasing the angle α, the cylinder 23 is positioned in the holes 25, 26 that are the farthest from the pivot connection.

As a variant, only one of the supports 3, 5 is equipped with a series of holes. In this case, the angle α is adjusted by moving a single one of the ends of the cylinder 23 into the different holes of the series.

As a variant, the cylinder 23 could be replaced by an air flange 27 that is shown in broken lines in FIG. 3, attached, on the one hand, to the support 3 and, on the other hand, to the support 5. The angle α can be adjusted by adapting the amount of air to the inside of the chamber 27. Thus, the angle α can be increased by inflating the flange 27 and decreased by deflating the flange 27.

As a variant, it is possible to use any damping system that makes it possible to bend the knee. Thus, the flange 27 can be replaced by a part made of carbon or any other flexible material that may or may not comprise a hinge. As a variant, the thigh support 5 and the calf support 3 and, if necessary, the boot, are made of a single block without a hinge between the two supports (thigh boot type), with the material of this block playing the role of hinge and damper at the articulation between the calf and the thigh.

FIG. 5 shows skis 29 that are preferably used with the boot 1 according to the invention. These skis 29 are connected to one another by means 30, such as a small chain or a cord, making it possible to limit the gap between the skis, so as to prevent the risks of gap of the skis.

As a variant, in a simplified embodiment, the thigh support 5 forms a stationary angle α relative to the calf support 3 and is connected rigidly to the calf support 3, with the piston 23 being able, if necessary, to be replaced by a rigid bar. Even in this simplified variant, the boot 1 according to the invention makes it possible to support a portion of the weight of the skier, the latter able to rest on the supports 3 and 5 that are attached to the shell of the boot 1. By contrast, the suspension effect is lost. In addition, it is observed that holding the skier's knee inside the supports 3 and 5 protects it from a possible injury.

FIG. 4 shows a variant embodiment of the boot 1 according to the invention that is designed for individuals having problems moving their abdominal part. More specifically, in this variant, the boot 1 also comprises a lumbar belt 33 that is connected to the leg support 5 by means of a cylinder 34 that makes it possible to hold the top of the skier's body. In this embodiment, the entire top of the skier's body can be supported on the support 3 and/or the support 5. All of the above-mentioned systems implemented between the calf and the thigh are applied in the same way between the thigh and the abdomen.

FIGS. 6a and 6 respectively show a side view and a top view of a ski 29 that comprises a gliding pad 29.1 on which are mounted a front attachment 29.2 and a rear attachment 29.3 that are designed to accommodate respectively the front part 36 of the ski boot and the rear part 37 of the ski boot.

In the ski according to the invention, the front attachment 29.2 is connected by a hinge-type mobile system 39 that has an axis 39.1 that is perpendicular to the direction of elongation of the ski (this axis 39.1 is perpendicular to the sheet in FIG. 6a). Thus, an individual having problems getting back up can, after having taken off his skis, bring his skis 29 under his body at the same time that he brings his feet back under him (since the skis are connected to the boot via the hinge 39), lean toward the front by placing his knees on the front of the skis 29, and push on his arms to get back up in such a way that the boot 1 can pivot around the axis 39.1 and take its place again inside the attachments 29.2, 29.3.

In certain embodiments, the hinge 39 can be removable. For this purpose, its axis is formed by a pin or a rod having radial extensions mounted on springs, which makes it possible to disengage the boot 1 from its ski 29.

As a variant, the hinge 39 can be replaced by a ball-joint connection. The use of a hinge or ball-joint system is, of course, independent of the use of the system for limiting the gap of the skis in such a way that it can be used alone or in combination with this system.

The invention claimed is:

1. A ski boot (1), comprising:
an inner boot (1.1) that is designed to accommodate the skier's foot;
a leading shell (1.2) that surrounds the inner boot (1.1), making it possible to hold the skier's ankle in place;
a calf support (3) attached to the shell (1.2) that is designed to accommodate the skier's calf;
a thigh support (5) that forms an angle (α) with the calf support (3) that is designed to accommodate the skier's thigh when the latter is in the bent position,
wherein the calf support (3) and the thigh support (5) are arranged between one another in such a way as to be able to support a portion of the skier's body; and
means (25, 26) for adjusting the bending angle (α) between the calf support (3) and the thigh support (5) formed by a series of holes (25, 26) made along at least one of i) the length of the calf support (3) and ii) the length of the thigh support (5), wherein the ends of the cylinder (23) can each engage in one of the holes (25, 26).

2. Ski boot according to claim 1, wherein the further comprising a damping means formed by a double-action cylinder (8) that has one end (8.1) that is linked in rotation to the calf support (3) or the shell (1.1) of the boot and one end (8.2) that is linked in rotation to the thigh support (5), whereby this cylinder (8) is supplied by a compressed air distribution circuit.

3. Ski boot according to claim 2, wherein a control means of the compressed air distribution circuit are control buttons (19, 20) or voice recognition means.

4. Ski boot according to claim 1, further comprising a damping means formed by a single-action cylinder that makes it possible to raise the thigh support (5) by the compressed air intake, with the cylinder then being lowered by the weight of the skier's body that expels air from the cylinder.

5. Ski boot according to claim 1, further comprising a damping means (23) formed by a cylinder (23) that is inflated in advance to a determined pressure with nitrogen or any other gas.

6. A ski boot (1), comprising:
an inner boot (1.1) that is designed to accommodate the skier's foot;
a leading shell (1.2) that surrounds the inner boot (1.1), making it possible to hold the skier's ankle in place;
a calf support (3) attached to the shell (1.2) that is designed to accommodate the skier's calf; and
a thigh support (5) that forms an angle (α) with the calf support (3) that is designed to accommodate the skier's thigh when the latter is in the bent position,
wherein the calf support (3) and the thigh support (5) are arranged between one another in such a way as to be able to support a portion of the skier's body, and
wherein the thigh support (5) is linked in movement relative to the calf support (3);
a damping means (8, 23, 27) that is installed between the shell (1.2) of the boot or the calf support (3), and the thigh support (5), wherein the damping means is formed by an air flange (27) or any other flexible rod that is attached to the calf support (3) and to the thigh support (5).

7. Ski boot according to claim 6, further comprising means (25, 26) for adjusting the bending angle (α) between the calf support (3) and the thigh support (5).

8. Ski boot according to claim 6, further comprising means (25, 26) for adjusting the bending angle (α) between the calf support (3) and the thigh support (5), and said means for adjusting the angle (α) between the calf support (3) and the thigh support (5) being formed by a series of holes (25, 26) made along the length of the calf support (3) and/or along the length of the thigh support (5), whereby the ends of the cylinder (23) can each engage in one of the holes (25, 26).

9. Ski boot according to claim 6, wherein it is made of a single block with the thigh support (5) and the calf support (3) without a hinge between the two supports in such a way as to form a thigh boot, whereby the material of this block plays the role of hinge and damper.

10. Ski boot according to claim 6, wherein the calf support (3) and the thigh support (5) are equipped with at least one fabric strap (3.3, 5.3) for holding respectively the tibia and the thigh of the skier in a position inside the supports (3, 5).

11. Ski boot according to claim 6, wherein the calf support (3) rises as close as possible to the articular center of the knee.

12. Ski boot according to claim 6, wherein the calf support (3) is over-molded on the shell (1.2) of the boot (1) or molded together with the shell.

13. Ski boot according to claim 6, wherein it also comprises a lumbar belt (33) linked to the thigh support (5) or to the calf support (3).

14. Ski boot according to claim 6 in combination with skis (29) that comprise means for limiting a gap between the skis.

15. The combination according to claim 14, where the skis comprising a gliding blade (29.1) on which are mounted a front attachment (29.2) and a rear attachment (29.3) that are designed to accommodate respectively the front part (36) of the ski boot and the rear part (37) of the ski boot (1), wherein the front attachment (29.2) is connected by a hinge- or ball-joint-type mobile system (39) to the boot (1) for making it possible to lift the individual up again after a fall.

16. A ski boot (1), comprising:
an inner boot (1.1) that is designed to accommodate the skier's foot;
a leading shell (1.2) that surrounds the inner boot (1.1), making it possible to hold the skier's ankle in place;
a calf support (3) attached to the shell (1.2) that is designed to accommodate the skier's calf;
a thigh support (5) that forms an angle (α) with the calf support (3) that is designed to accommodate the skier's thigh when the latter is in the bent position,
wherein the calf support (3) and the thigh support (5) are arranged between one another in such a way as to be able to support a portion of the skier's body, and
wherein the thigh support (5) is linked in movement relative to the calf support (3),
wherein the damping means (23) is formed by a cylinder (23) that is inflated in advance to a determined pressure with nitrogen or any other gas; and
means (25, 26) for adjusting the bending angle (α) between the calf support (3) and the thigh support (5), said means for adjusting the angle (α) between the calf support (3) and the thigh support (5) being formed by a series of holes (25, 26) made along the length of the calf support (3) and/or along the length of the thigh support (5), whereby the ends of the cylinder (23) can each engage in one of the holes (25, 26).

17. Ski boot according to claim 16, wherein the cylinder is a double-action cylinder (8) that has one end (8.1) that is linked in rotation to the calf support (3) or the shell (1.1) of the boot and one end (8.2) that is linked in rotation to the thigh support (5), whereby this cylinder (8) is supplied by a compressed air distribution circuit.

\* \* \* \* \*

UNITED STATES PATENT AND TRADEMARK OFFICE
CERTIFICATE OF CORRECTION

PATENT NO. : 8,714,567 B2  Page 1 of 1
APPLICATION NO. : 13/202672
DATED : May 6, 2014
INVENTOR(S) : Hubert Fievet It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 34 days.

Signed and Sealed this
Twenty-ninth Day of September, 2015

Michelle K. Lee
*Director of the United States Patent and Trademark Office*